United States Patent [19]
Ayers et al.

[11] Patent Number: 5,549,641
[45] Date of Patent: Aug. 27, 1996

[54] ATRIAL FIBRILLATION TYPE SELECTIVE CARDIOVERTOR AND METHOD

[75] Inventors: Gregory M. Ayers, Duvall; Clifton A. Alferness, Redmond, both of Wash.

[73] Assignee: InControl, Inc., Redmond, Wash.

[21] Appl. No.: 331,898

[22] Filed: Oct. 31, 1994

[51] Int. Cl.⁶ .................................................. A61N 1/39
[52] U.S. Cl. ..................................................... 607/4; 607/5
[58] Field of Search ............................. 607/4, 5; 128/705, 128/702

[56] References Cited

U.S. PATENT DOCUMENTS

| | | | |
|---|---|---|---|
| 4,872,459 | 10/1989 | Pless et al. ............................... | 128/705 |
| 5,107,850 | 4/1992 | Olive ........................................ | 128/705 |
| 5,205,283 | 4/1993 | Olson ........................................ | 607/4 |
| 5,342,402 | 8/1994 | Olson et al. ................................ | 607/5 |
| 5,439,483 | 8/1995 | Duong-Van ................................ | 607/5 |

OTHER PUBLICATIONS

*Characterization of Atrial Fibrillation in Man: Studies Following Open Heart Surgery*, Wells, Jr. et al., Pace, vol. 1, Oct. –Dec., 1978, pp. 426–438.

Abstract: *Effects of β–Methacholine on the Atria: Implications for Understanding Atrial Fibrillation and Transvenous Atrial Defibrillation*, Ortiz et al., NASPE 15th Annual Scientific Sessions Abstract Form, submitted Nov. 30, 1993.

Primary Examiner—William E. Kamm
Assistant Examiner—Kennedy J. Schaetzle
Attorney, Agent, or Firm—Richard O. Gray, Jr.

[57] ABSTRACT

An atrial cardiovertor/defibrillator provides therapy to the atria corresponding to the type of atrial arrhythmia occurring in the atria of the heart. The atrial cardiovertor/defibrillator includes a memory for storing respective different criteria for each of different types of atrial arrhythmia, a sensor for sensing activity of at least one of the atria of the heart to provide an electrogram signal, and a cardiovertor for providing a corresponding therapy to the heart for each of the different types of atrial arrhythmia. The cardiovertor/defibrillator further includes an atrial arrhythmia detector responsive to the electrogram signal and the stored criteria for identifying one of the types of atrial arrhythmia to cause the cardiovertor to provide therapy to the heart corresponding to the identified atrial arrhythmia.

56 Claims, 3 Drawing Sheets

ATRIAL FIBRILLATION TYPE SELECTIVE CARDIOVERTOR AND METHOD

BACKGROUND OF THE INVENTION

The present invention generally relates to an atrial cardiovertor/defibrillator and method for applying cardioverting electrical energy to the atria of a human heart in need of cardioversion. The present invention is more particularly directed to an improved atrial cardiovertor/defibrillator which provides cardioversion therapy corresponding to the relative degree of organization/disorganization of a detected atrial arrhythmia.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness as a result of reduced cardiac output.

Atrial fibrillation occurs suddenly, and many times can only be corrected by an external defibrillator discharging electrical energy to the heart through the skin of the patient. This treatment is commonly referred to as synchronized cardioversion and, as its name implies, involves applying electrical defibrillating energy to the heart in synchronism with a detected R wave of the heart. The treatment is very painful and, unfortunately, most often provides patients only with temporary relief lasting but a few weeks to months.

Drugs are available for reducing the incidence of atrial fibrillation. However, these drugs have many side effects and many patients are resistant to them, which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality. Two such proposed defibrillators, although represented as being implantable, were not fully automatic, require human interaction for cardioverting or defibrillating the heart. Both of these proposed defibrillators require the patient to recognize the symptoms of atrial fibrillation, with one defibrillator requiring a visit to a physician to activate the defibrillator, and the other defibrillator requiring the patient to activate the defibrillator with an external magnet.

An improved atrial defibrillator and lead system which is fully automatic in operation is described in U.S. Pat. No. 5,282,837, which issued on Feb. 1, 1994, for ATRIAL DEFIBRILLATOR AND METHOD, which patent is assigned to the assignee of the present invention and incorporated herein by reference. The defibrillator described in the aforementioned referenced patent automatically detects the presence of an atrial fibrillation episode and applies cardioverting electrical energy to the atria in timed relation to a sensed R wave of the heart. Ventricular pacing is also provided by the described defibrillator.

As can be noted from the above, atrial defibrillators that are currently known detect for the simple presence and absence of atrial fibrillation. If atrial fibrillation is detected, a single therapy regimen is employed. While such devices will provide much needed relief to many patients suffering from atrial fibrillation, further improvements are possible. One such improvement is addressed herein.

It has been observed that atrial activity associated with atrial arrhythmias can vary in organization from highly organized activity to highly disorganized activity. Atrial flutter, for example, is a highly organized atrial arrhythmia. Atrial activity of increasing disorganization, beyond atrial flutter, is generally referred to as atrial fibrillation. Atrial arrhythmias, therefore, encompass a wide range of organization and disorganization from atrial flutter, which is highly organized, to atrial fibrillation, which itself encompasses a wide range of atrial activity organizational characteristics, from what may be referred to as atrial activity of intermediate organization to atrial activity of high disorganization. Recognizing these atrial arrhythmia characteristics, Wells, Jr. et al. in Characterization of trial Fibrillation in Man: Studies Following Open Heart Surgery, *Pace,* Vol. 1, pp. 426–438, October–December, 1978, type characterized various forms of atrial fibrillation and further reported that the atria, during an arrhythmic episode, can transition between the characterized forms of atrial arrhythmias and can even self-revert to normal sinus rhythm. In addition to the above, it has been more recently learned through research sponsored by the assignee of the present invention that the amount of cardioverting electrical energy required to cardiovert an atrial arrhythmia to return the atria to a normal rhythm increases as the degree of disorganization in atrial activity increases during an arrhythmic episode.

While atrial defibrillators which detect the simple presence and absence of atrial fibrillation (including atrial flutter) and which provide a single intervention regimen if atrial fibrillation is detected will provide needed relief for many patients, these devices for some patients exhibit certain deficiencies. For example, the single intervention regimen can result in a greater amount of electrical energy being applied to the atria than needed to successfully cardiovert the atria. This can submit the patient to a higher degree of potential discomfort than would otherwise be necessary. It can also result in a greater than necessary consumption of battery power which would ultimately shorten the useful life of the cardioverting device. As another example, and at the other end of the organization spectrum, the atrial activity may be so disorganized that the implanted defibrillator is incapable of providing a sufficient amount of energy to cardiovert the atria. Where a single intervention regimen is utilized, therefore, cardioversion would still be attempted with a quantity of cardioverting energy which is less than that required to cardiovert the atria. This would also submit the patient to therapy destined to be ineffective and, hence, therapy which should not be applied, while wasting precious battery power.

The present invention overcomes the previously noted disadvantages in the art by tailoring atrial arrhythmia intervention in accordance with a type classification of the arrhythmia from among a plurality of atrial arrhythmia types. In accordance with one aspect of the present invention, an atrial arrhythmia may be classified as atrial flutter having a high degree of organization, atrial fibrillation having an intermediate degree of organization (type 1), or atrial fibrillation having a high degree of disorganization (type 2). In accordance with another aspect of the present invention, therapy for atrial flutter is provided by atrial pacing or low energy cardioversion and therapy for atrial fibrillation of intermediate organization is provided by medium energy cardioversion. Therapy for atrial fibrillation of high disorganization includes delaying cardioversion for a pre-set time period to permit the atrial activity to potentially transition to atrial fibrillation of intermediate disorganization, whereupon medium energy cardioversion is provided. If the atrial activity does not transition during the pre-set time period, cardioversion of comparatively high energy is provided.

In accordance with another aspect of the present invention, the degree of organization/disorganization of the atrial arrhythmia is determined by atrial cardiac cycle length alone or in combination with atrial cardiac cycle length variability. The atrial cardiac cycle length is determined from the detection of localized activity in one of the atria, such as the right atrium, using a closely spaced bi-polar pair of sensing electrodes.

As will be seen hereinafter, the present invention therefore results in therapy being administered to the patient which is in keeping with the particular type of atrial arrhythmia being experienced by the patient. The present invention therefore provides an improved atrial defibrillator which exhibits significant advantages over prior art atrial defibrillators. Such advantages include a reduction in unnecessary or ineffective cardioversion attempts, less potential discomfort to patients, and the avoidance of unduly shortening the lifetime of an implanted defibrillator.

SUMMARY OF THE INVENTION

The present invention therefore provides an atrial cardiovertor/defibrillator including criteria establishing means for providing a respective different criteria for each of different types of atrial arrhythmia, a sensor for sensing activity of at least one of the atria of a heart to provide an electrogram signal, and therapy means for providing a corresponding therapy to the heart for each of the different types of atrial arrhythmia. The atrial cardiovertor/defibrillator further includes classifying means responsive to the electrogram signal and the criteria establishing means for identifying one of the types of atrial arrhythmia and causing the therapy means to provide the therapy to the heart corresponding to the identified one of the types of atrial arrhythmia.

The present invention further provides an atrial defibrillator including criteria establishing means for providing a respective different criteria for each of different types of atrial fibrillation, a sensor for sensing activity of at least one of the atria of a heart to provide an electrogram signal, and therapy means for providing a corresponding therapy to the heart for each of the different types of atrial fibrillation. The atrial defibrillator further includes classifying means responsive to the electrogram signal and the criteria establishing means for identifying one of the types of atrial fibrillation and causing the therapy means to provide the therapy to the heart corresponding to the identified one of the types of atrial fibrillation.

The present invention further provides a method of administering electrotherapy to the atria of a patient's heart to restore a normal atrial rhythm. The method includes the steps of establishing a respective different criteria for each of different types of atrial arrhythmia, sensing activity of at least one of the atria of a patient's heart to provide an electrogram signal, applying the electrogram signal to each criteria to identify one of the types of atrial arrhythmia, and applying electrotherapy to the heart in a manner corresponding to the identified one of the types of atrial arrhythmia.

The present invention still further provides a method of administering electrotherapy to the atria of a patient's heart to restore a normal atrial rhythm from fibrillation. The method includes the steps of establishing a respective different criteria for each of different types of atrial fibrillation, sensing activity of at least one of the atria of the patient's heart to provide an electrogram signal, comparing at least one characteristic of electrogram signal to each criteria and identifying from the comparison one of the types of atrial fibrillation, and applying electrotherapy to the heart in a manner corresponding to the identified one of the types of atrial fibrillation.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements and wherein:

DETAILED DESCRIPTION OF THE PREFERRED EMBODIMENT

Figure 1:
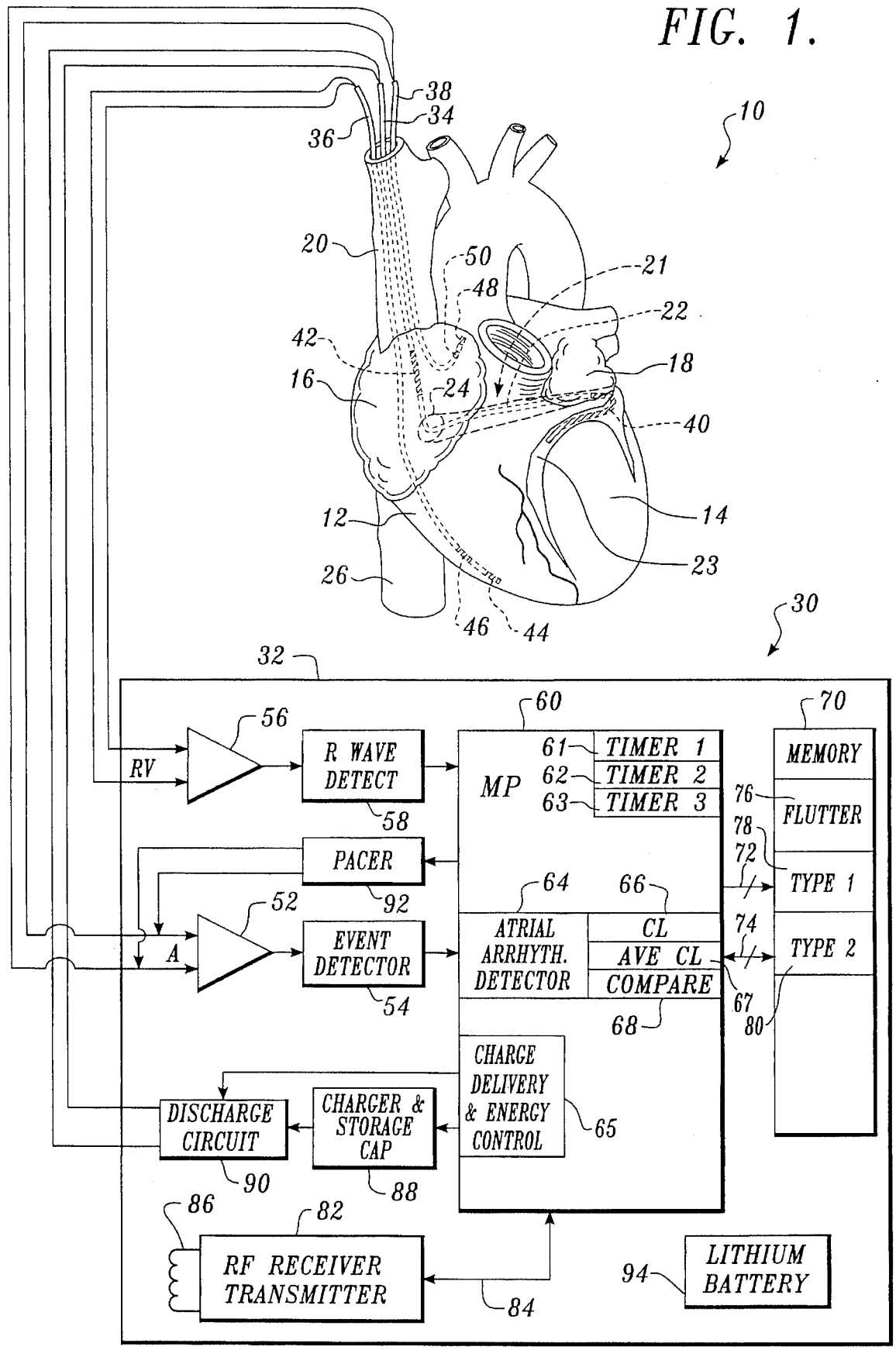
FIG. 1 is a schematic block diagram of a fully implantable atrial cardiovertor/defibrillator embodying the present invention, shown in association with a human heart in need of atrial arrhythmia monitoring and potential cardioversion.

Referring now to FIG. 1, it illustrates a fully implantable atrial cardiovertor/defibrillator 30 embodying the present invention shown in association with a schematically illustrated human heart 10 in need of atrial arrhythmia monitoring and potential cardioversion. The portions of the heart 10 illustrated in the FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 26.

The atrial cardiovertor/defibrillator 30 generally includes an enclosure 32 for hermetically sealing the internal circuit elements of the atrial cardiovertor/defibrillator, to be described hereinafter, an intravascular lead 34, a first endocardial lead 36, and a second endocardial lead 38. The enclosure 32 and the leads 34, 36 and 38 are arranged to be implanted beneath the skin of a patient so as to render the atrial cardiovertor/defibrillator 30 fully implantable.

The intravascular lead 34 generally includes a first or tip elongated electrode 40, and a second or proximal elongated electrode 42. As illustrated, the lead 34 is flexible and arranged to be passed down the superior vena cava 20, into the right atrium 16, into the coronary sinus ostium 24, and advanced into the coronary sinus channel 21 of the heart near the left side thereof, so that the electrode 40 is within the coronary sinus channel 21 either within the coronary sinus 22 adjacent the left ventricle 14 and beneath the left atrium 18, or most preferably within the great cardiac vein 23 beneath the left atrium 18. The electrodes 40 and 42 are spaced apart such that when the first electrode 40 is positioned as described above, the second electrode 42 is in the right atrium 16. The first electrode 40 together with the second electrode 42 provide for the delivery of cardioverting/defibrillating electrical energy to the atria, in a manner to be described subsequently.

The first endocardial lead 36 preferably includes a bi-polar pair of electrodes 44 and 46, arranged for establishing electrical contact with the right ventricle 12 of the heart 10. The electrodes 44 and 46 permit bi-polar sensing of ventricular activations (R waves) in the right ventricle. As illustrated, the lead 36 is fed through the superior vena cava 20, into the right atrium 16, and then into the right ventricle 22.

The second endocardial lead 38 also preferably includes a bi-polar pair of electrodes 48 and 50, arranged for establishing electrical contact with the right atrium 16 of the heart 10. The electrodes 48 and 50 are closely spaced apart for sensing localized activity of the right atrium. As illustrated, the lead 38 is fed through the superior vena cava 20, into the right atrium 16. The distal end of the lead 38 is substantially "J" shaped in a manner know in the art to position electrodes 48 and 50 in the appendage of the right atrium.

Within the enclosure 32, the atrial cardiovertor/defibrillator 30 includes a first sense amplifier 52, an atrial event detector 54, a second sense amplifier 56, and an R wave detector 58. The first sense amplifier 52 forms a first sensing means which, together with the electrodes 48 and 50 of the second endocardial lead 38 to which sense amplifier 52 is coupled, senses localized activity of the right atrium 16 to provide an electrogram signal to the atrial event detector 54. The second sense amplifier 56 forms a second sensing means which, together with electrodes 44 and 46 of the first endocardial lead 36 to which it is coupled, senses cardiac activity in the right ventricle of the heart to provide a second electrogram signal to the R wave detector 58.

The R wave detector 58 preferably includes a differentiating filter for differentiating the electrogram signal provided by sense amplifier 56. The R wave detector 58 further preferably includes a threshold circuit for setting an upper and lower threshold to provide an output when the upper or lower threshold is exceeded. The thresholds are set, as known in the art, so that only R waves will have sufficient amplitude to exceed the thresholds of the R wave detector.

The atrial event detector 54 similarly preferably includes a differentiating filter for differentiating the first electrogram signal, and a threshold circuit for setting an upper and lower threshold. When the differentiated first electrogram signal transitions beyond either the upper or lower threshold, the atrial event detector 54 provides an output indicating the occurrence of an atrial event.

The enclosure 32 of the atrial cardiovertor/defibrillator 30 further includes a microprocessor 60. The microprocessor 60 is preferably implemented in accordance with this embodiment of the present invention to result in a plurality of functional stages. The stages include a first timer 61, a second timer 62, and a third timer 63. The stages further include an atrial arrhythmia detector 64 and a charge delivery and energy control stage 65. The atrial arrhythmia detector 64 includes an atrial cycle length determining stage 66, an average cycle length determining stage 67, and a compare stage 68.

The microprocessor 60 is arranged to operate in conjunction with a memory 70 which is coupled to the microprocessor 60 by a multiple-bit address bus 72, and a bi-directional multiple-bit data bus 74. This permits the microprocessor 60 to address desired memory locations within the memory for executing write or read operations. During a write operation, the microprocessor stores data, such as atrial cycle lengths, or operating parameters, such as atrial arrhythmia type classifying criteria, in the memory at the addresses defined by multiple-bit addresses conveyed over the address bus 72, and conveys the operating parameters and data to the memory 70 over the multiple-bit data bus 74. During a read operation, the microprocessor 60 obtains data or operating parameters from the memory at the storage locations identified by the multiple-bit addresses provided over the address bus 72 and receives the operating parameters and data from the memory over the bi-directional data bus 74.

For entering programmable operating parameters into the memory 70, as for example, cardioverting or defibrillating peak voltages, or further, for example, atrial arrhythmia type classification criteria into memory portions 76, 78 and 80, the microprocessor 60 receives the programmable operating parameters from an external controller (not shown) which is external to the skin of the patient. The external controller may be arranged to communicate with a receiver/transmitter 82 within enclosure 32 which is coupled to the microprocessor 60 over a bi-directional bus 84. The receiver/transmitter 82 receives the programmable parameters from the external controller and then conveys the same to the microprocessor 60 for storage in memory 70. The receiver/transmitter 82 also conveys various information which it obtains from the microprocessor over bus 84 to the external controller.

The receiver/transmitter 82 includes a transmitting coil 86 so that the receiver/transmitter 82 and coil 86, together with the external controller, form a communication system. Such communication systems are well known in the art. One preferred communication system is disclosed in U.S. Pat. No. 5,342,408, which issued on Aug. 30, 1994, for "TELEMETRY SYSTEM FOR AN IMPLANTABLE CARDIAC DEVICE", which patent is assigned to the assignee of the present invention and incorporated herein by reference.

To complete the identification of the various structural elements within the enclosure 32, the atrial cardiovertor/defibrillator 30 further includes a charger and storage capacitor circuit 88 of the type well known in the art which charges a storage capacitor to a selected peak voltage, and a discharge circuit 90 for discharging the storage capacitor within circuit 88 for a predetermined time to provide a controlled discharge output of electrical energy to the atria of the heart when required. To that end, the discharge circuit 90 is coupled to electrodes 40 and 42 of the intravascular lead 34 for applying the cardioverting or defibrillating electrical energy to the atria. Lastly, the cardiovertor/defibrillator 30 includes a pacer 92 and a depletable power source 94, such as a lithium battery, for providing power to the electrical components of the atrial cardiovertor/defibrillator 30. The pacer 92 is coupled to the electrodes 48 and 50 to provide overdrive pacing of the atria, in a manner to be described hereinafter, when atrial flutter of the atria is detected.

Atrial arrhythmia type classification criteria are established in the memory 70 and more particularly in memory portions 76, 78 and 80. Memory portion 76 stores criteria for atrial flutter which is highly organized. Memory portion 78 stores criteria corresponding to atrial fibrillation of intermediate organization (type 1), and memory portion 80 stores criteria corresponding to atrial fibrillation of high disorganization (type 2). The degree of organization or disorganization can be determined by atrial cardiac cycle length alone, or in combination with a measure of atrial cardiac cycle length variability.

At predetermined times, determined by the first timer 61, the atrial arrhythmia detector 64 is activated to determine if an atrial arrhythmic episode is occurring in the atria, and to classify the arrhythmia if one is present. The atrial cycle length determining stage 66 determines, over a predetermined time or over a predetermined number of atrial cardiac cycles, the atrial cardiac cycle lengths of the heart, and stores the cycle lengths in memory 70. The atrial cardiac cycle lengths are the time spans between adjacent atrial events as identified by the atrial event detector 54. Once the cycle lengths are determined, an average cycle length is determined by the average cycle length determining stage 67. The average cycle length is then compared by the compare stage 68 to the atrial arrhythmia type classification criteria stored in memory portions 76, 78 and 80.

First, the microprocessor 60 accesses normal sinus rhythm criteria stored in memory 70 to determine if the atria are in normal sinus rhythm. More specifically, if the average cycle length is greater than a stored criteria of 250 milliseconds, for example, the atria are considered to be in normal sinus rhythm and, hence, an absence of atrial arrhythmia is considered to have been detected. If the atria are not in normal sinus rhythm and, hence, experiencing an arrhythmic episode, the type of atrial arrhythmia is then determined.

To determine the atrial arrhythmia type, the microprocessor 60 first accesses the memory portion 76 which establishes atrial flutter criteria. If the average atrial cardiac cycle length is less than 250 milliseconds, but greater than the 150 millisecond criteria stored in memory portion 76, the atria are considered to be in atrial flutter. A therapy corresponding to the detected atrial flutter is then applied to the atria, either by overdrive pacing or low energy cardioversion.

If the overdrive pacing therapy is selected by programming, the pacer 92 is activated by the atrial arrhythmia detector 64 to overdrive pace the atria in a manner well known in the art. The pacing pulses, to that end, are applied to the right atrium by electrodes 48 and 50.

If the low energy cardioversion therapy is selected by programming, the charge delivery and control stage 65 is activated by the atrial arrhythmia detector 64 to cause the capacitor of circuit 88 to be charged to a relatively low peak voltage of, for example, 80 volts. When the capacitor is charged, the charge delivery and energy control causes the discharge circuit 90 to discharge the capacitor of circuit 88 in timed relation to an R wave detected by sense amplifier 56 and R wave detector 58. The discharge circuit 90 discharges the capacitor of circuit 88 for a controlled period of time to provide the application of cardioverting energy to the atria across electrodes 40 and 42 of lead 34. By charging the capacitor to a voltage of 80 volts, low cardioverting energy in the range of 0.2 joule is applied to the atria for cardioverting the atrial flutter.

If the atria are not in atrial flutter, the microprocessor 60 then accesses the memory portion 78 which establishes a criteria for atrial fibrillation of intermediate organization. If the compare stage 68 determines that the average atrial cardiac cycle length is less than 150 milliseconds, but greater than 75 milliseconds, the atria are considered to be in atrial fibrillation of intermediate organization (type 1). A therapy corresponding to the type 1 atrial fibrillation is then applied to the atria. In accordance with this preferred embodiment, the therapy applied to the atria corresponding to the type 1 atrial fibrillation is atrial cardioversion or defibrillation of an intermediate energy range of between 0.5 joules and 2 joules. To apply this therapy, the capacitor of circuit 88 is charged as previously described, and the charge delivery and energy control 65 causes the discharge circuit 90 to discharge the capacitor in timed relation to a sensed R wave, as previously described.

If the atria are not in type 1 atrial fibrillation, the microprocessor 60 may then access memory portion 80 to enable the compare stage 68 to determine if the average atrial cardiac cycle length satisfies the criteria for type 2 atrial fibrillation. To satisfy this criteria, in accordance with this embodiment, the average atrial cardiac cycle length must be less than 75 milliseconds. If it is, the atrial fibrillation is considered to be highly disorganized and a further and different therapy regimen than that previously described will be invoked. This therapy regimen will be described in detail hereinafter with respect to the flow diagram of FIG. 3. As will be seen hereinafter with respect to the preferred embodiment of FIG. 2, this last compare may be eliminated. However, it is included here for completeness because confirmation of the type 2 atrial fibrillation may be desirable before invoking the therapy of FIG. 3.

Figure 2:
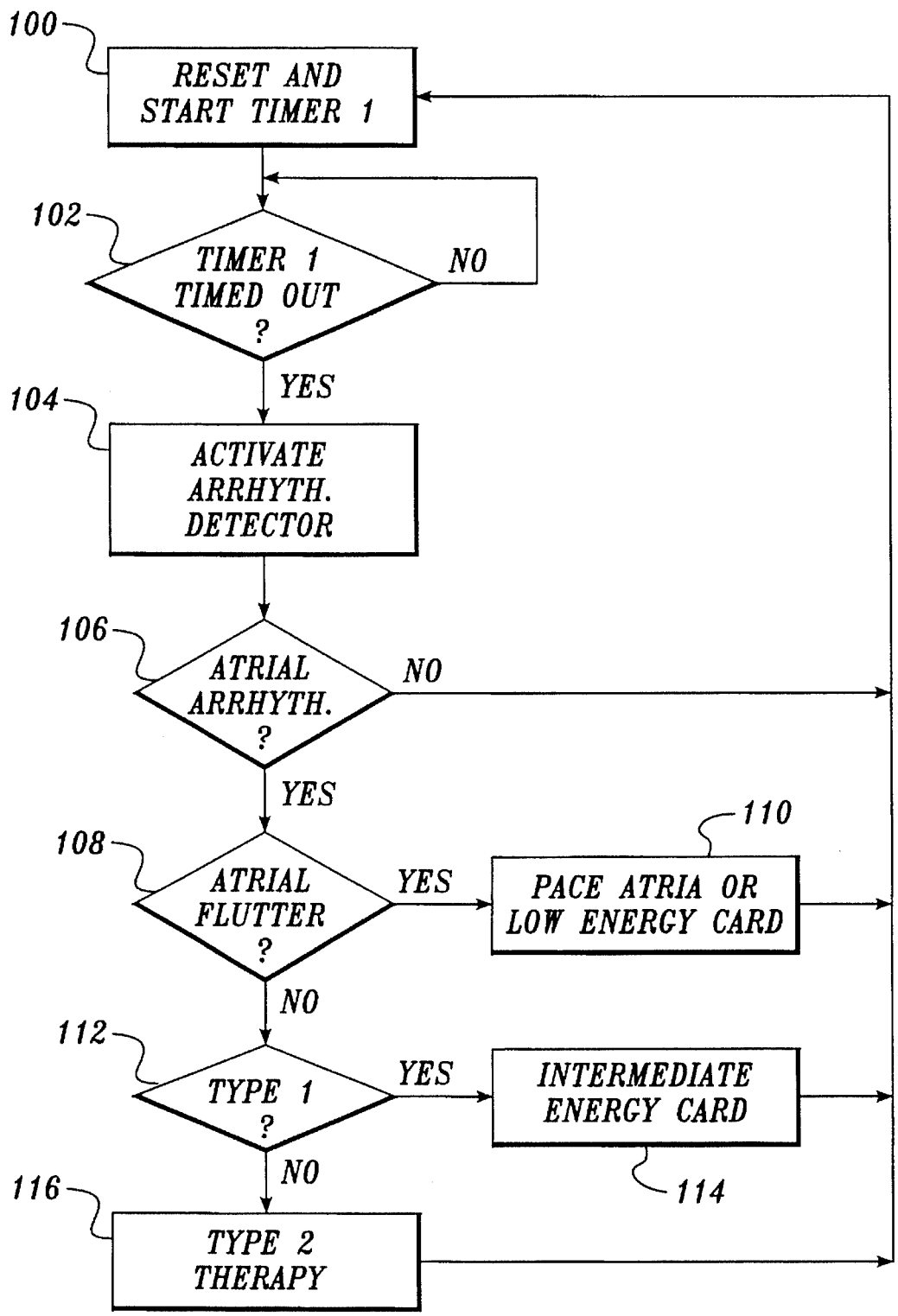
FIG. 2 is a flow diagram illustrating the manner in which the atrial cardiovertor/defibrillator of FIG. 1 may be implemented to identify atrial arrhythmia type and provide corresponding cardioversion therapy; and, FIG. 3 is a flow diagram illustrating the manner in which the atrial cardiovertor/defibrillator of FIG. 1 may be implemented to provide intervention therapy for atrial fibrillation of high disorganization.

Referring now to FIG. 2, it illustrates, in flow diagram form, the manner in which the atrial cardiovertor/defibrillator 30 of FIG. 1 may be implemented to identify an atrial arrhythmia type and provide corresponding cardioversion or defibrillation therapy. The process begins in step 100 wherein the first timer 61 is re-set and started. When it is determined in step 102 that the first timer 61 has timed out, the first timer 61 activates the atrial arrhythmia detector 64 in step 104.

Once the atrial arrhythmia detector is activated, the atrial arrhythmia detector 64 first determines if the atria are experiencing an arrhythmic episode in accordance with step 106. As previously described, if the average atrial cardiac cycle length is greater than 250 milliseconds, the atria will be considered to be in normal sinus rhythm, whereupon the process returns to step 100 to re-set and start the first timer 61. However, if the average atrial cardiac cycle length is less than 250 milliseconds, the process then proceeds to step 108, wherein it is determined if the atria are in atrial flutter. As previously described, if the atrial cardiac cycle length is greater than 150 milliseconds and less than 250 milliseconds, the atria will be considered to be in atrial flutter. As a result, in step 110, therapy is applied by either overdrive pacing or low energy cardioversion of the atria.

If it is determined in step 108 that the atria are not in atrial flutter, the process then proceeds to step 112 to determine if the atria are in type 1 atrial fibrillation. As previously described, if the average atrial cardiac cycle length is greater than 75 milliseconds, and less than 150 milliseconds, the atria will be considered to be in type 1 atrial fibrillation, which is atrial fibrillation of intermediate organization. If such a determination is made, the process then proceeds to step 114 to provide therapy corresponding to the type 1 atrial fibrillation, as previously described, by applying cardioverting or defibrillating electrical energy to the atria having an intermediate energy of between 0.5 joules and 2 joules, for example.

If the atria are not in atrial flutter, or in type 1 atrial fibrillation, it is then assumed that the atria are in type 2 atrial fibrillation. The process then, in accordance with step 116, proceeds to the therapy illustrated in FIG. 3

Figure 3:
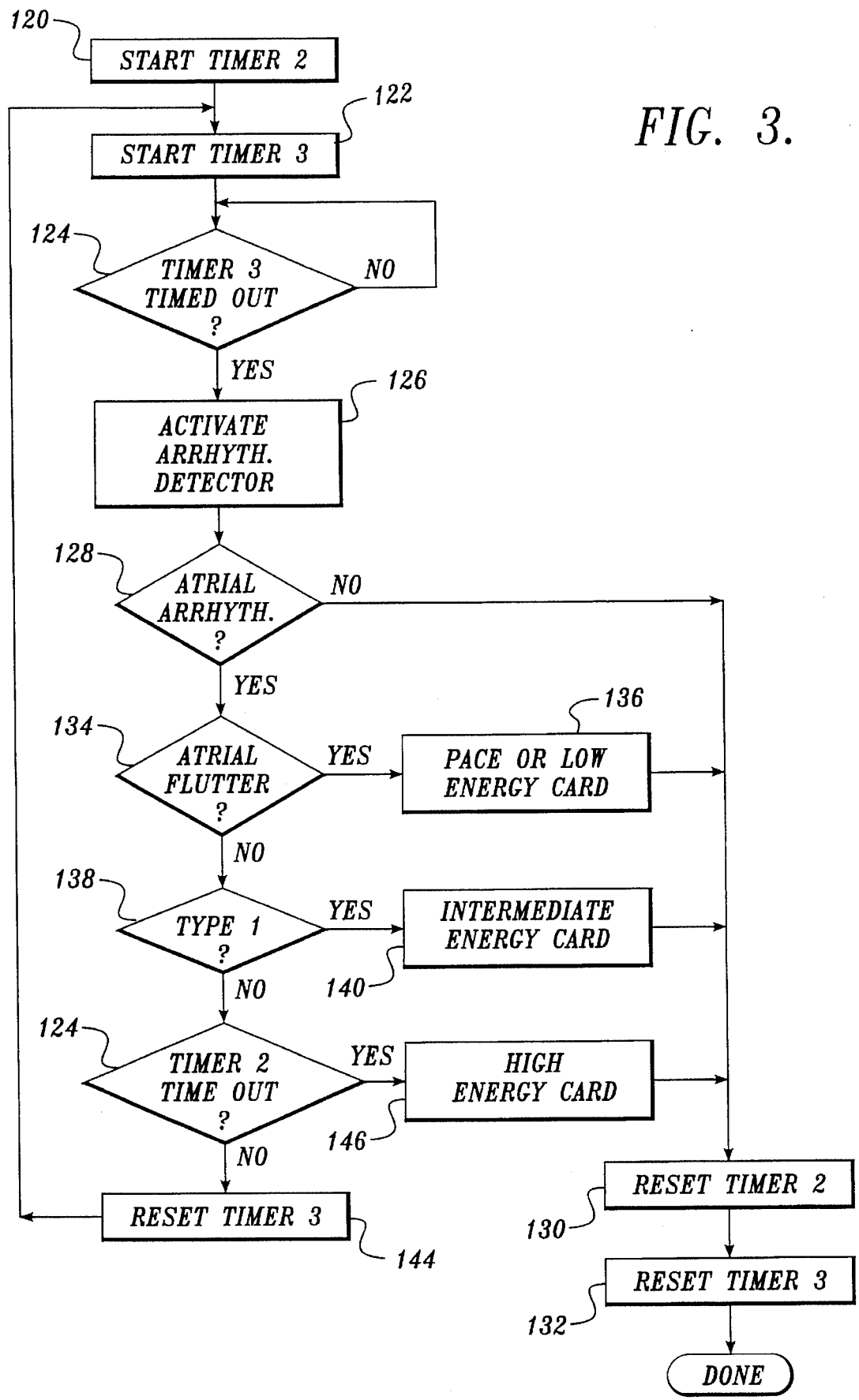

Referring now to FIG. 3, it illustrates in flow diagram form the manner in which the atrial cardiovertor/defibrillator 30 of FIG. 1 may be implemented to provide intervention therapy for atrial fibrillation of high disorganization (type 2).

The process first begins by starting the second timer 62 in accordance with step 120. Next, in step 122, the third timer 63 is started. The second timer 62 times a pre-set time period of, for example, one hour, whereas the third timer 63 times a time period which is much shorter in length than the pre-set time period. The time period timed by the third timer 63 may be, for example, five minutes.

When the third timer times out as determined in step 124, the atrial arrhythmia detector 64 is once again activated in step 126. The atrial arrhythmia detector first determines in step 128 if the atria are still experiencing an arrhythmic episode. If the atria have self-reverted to normal sinus rhythm, the process then proceeds to step 130 by resetting the second timer 62, and then proceeds to step 132 to re-set the third timer 63. Once the third timer 63 is re-set in step 132, the intervention therapy is completed.

If, in step 128, it is determined that the atria are still in an arrhythmic episode, the atrial arrhythmia detector 64 will first determine if the atria are in atrial flutter in accordance with step 134, as previously described. If the atrial arrhythmia has self-reverted to atrial flutter, the process then proceeds to step 136 to provide therapy corresponding to atrial flutter which includes either overdrive pacing or low energy cardioversion of the atria. Once the intervention therapy is completed in accordance with step 136, steps 130 and 132 are repeated, as previously described, and the intervention therapy is completed.

If, in step 134, it is determined that the atria are not in atrial flutter, the process then proceeds to step 138 to determine if the type 2 atrial fibrillation has transitioned to the more organized type 1 atrial fibrillation. If the atria have transitioned to the type 1 atrial fibrillation, the process then proceeds to step 140 to apply the therapy corresponding to the type 1 atrial fibrillation, which includes the application of cardioverting or defibrillating electrical energy to the atria at an energy level of between 0.5 joules and 2 joules, for example. Once the therapy is completed in accordance with step 140, steps 130 and 132 are repeated, as previously described, and the therapy is completed.

If the atria have not transitioned to the more organized type 1 atrial fibrillation as determined in step 138, the process then proceeds to step 142 to determine if the second timer 62 has timed out. If the second timer has not timed out, the third timer 63 is then re-set in step 144 and the process returns to start the third timer 63 at step 122. However, if the second timer 62 has timed out, as determined in step 142, the process then proceeds to step 146 to provide defibrillating energy to the atria at a relatively high energy level to defibrillate or cardiovert the atria. In providing the intervention therapy of step 146, an energy level of greater than 2 joules and, preferably, on the order of 3 joules may be utilized for cardioverting the atria. Although not illustrated in FIG. 3, it may be preferable to reconfirm the type 2 atrial fibrillation prior to performing step 146. When the intervention therapy is completed in accordance with step 146, steps 130 and 132 are repeated, as previously described, and the therapy is completed.

As a result, as can be seen from FIG. 3, if it is determined that the atria are in the type 2 atrial fibrillation, which is atrial fibrillation of high disorganization requiring a therapy of relatively high energy cardioversion, the application of the cardioverting energy is delayed for a pre-set period of time of, for example, one hour to permit the atria to transition to a more organized form of atrial fibrillation, requiring lesser energy to successfully cardiovert the arrhythmic episode. The atrial activity is examined every five minutes, for example, during the pre-set time, to determine if the atria have self-reverted to a more organized form of atrial fibrillation. However, if at the end of the pre-set time of, for example, one hour, the atria have not self-reverted to a more organized form of atrial fibrillation, the atrial cardiovertor/defibrillator 30 will then provide atrial fibrillation therapy at the relatively high energy.

While in accordance with this preferred embodiment the degree of organization or disorganization of the atrial activity is determined by atrial cardiac cycle length alone, atrial cardiac cycle length variability may also be used in combination therewith for classifying the type of atrial arrhythmic episode. If such variability is employed, the compare stage 68 may compare each determined atrial cardiac cycle length to the average cycle length. The maximum difference therebetween may then be used as the degree of variability for further defining the atrial arrhythmia type. The relative degree of organization/disorganization may also be determined through the use of correlation functions applied, for example, to the atrial activity sensed at different areas of the atria. Such correlation functions are well known in the art.

In addition, although real time processing of the atrial activity to determine the atrial cardiac cycle lengths is contemplated by this preferred embodiment, it will be appreciated by those skilled in the art that such determinations may be made from data stored in memory during a data acquisition period prior to the atrial arrhythmia detector being activated for operating on the stored data to determine the atrial cardiac cycle lengths, the average cycle length, and the maximum variance between the cycle lengths and the average cycle length. Hence, while a particular embodiment of the present invention has been shown and described, modifications may be made and it is therefore intended in the appended claims to cover all such changes and modifications which fall within the true spirit and scope of the invention.

What is claimed is:

1. An atrial cardiovertor/defibrillator comprising:

criteria establishing means for providing a respective different criteria for each of different types of atrial arrhythmia;

a sensor for sensing activity of at least one of the atria of a heart to provide an electrogram signal;

therapy means for providing a corresponding therapy to the heart for each of said different types of atrial arrhythmia; and classifying means responsive to said electrogram signal and said criteria establishing means for identifying one of said types of atrial arrhythmia and causing said therapy means to provide the therapy to the heart corresponding to said identified one of said types of atria arrhythmia, wherein the respective different criteria include a first criteria for atrial flutter, a second criteria for atrial fibrillation of intermediate organization, and a third criteria for atrial fibrillation of high disorganization.

2. An atrial cardiovertor/defibrillator as defined in claim 1 wherein the therapy means comprises an atrial pacer and an atrial cardiovertor.

3. An atrial cardiovertor/defibrillator as defined in claim 2 wherein said classifying means causes said atrial pacer to pace the atria upon identifying atrial flutter.

4. An atrial cardiovertor/defibrillator as defined in claim 3 wherein said classifying means causes said cardiovertor to apply cardioverting electrical energy to the atria at an intermediate energy level upon identifying atrial fibrillation of intermediate disorganization.

5. An atrial cardiovertor/defibrillator as defined in claim 4 wherein said classifying means causes said cardiovertor to apply cardioverting electrical energy to the atria at a high energy level upon identifying atrial fibrillation of high disorganization, said high energy level being greater in energy than said intermediate energy level.

6. An atrial cardiovertor/defibrillator as defined in claim 5 further including first means for causing said cardiovertor to delay the application of the high energy level cardioverting energy for a pre-set time period.

7. An atrial cardiovertor/defibrillator as defined in claim 6 further including second means for activating said classifying means at predetermined times during said pre-set time period, said classifying means causing said cardiovertor to apply said intermediate energy level cardioverting energy upon identifying, during said pre-set time period, atrial fibrillation of intermediate disorganization and causing said cardiovertor to apply said high energy level cardioverting energy at the end of said pre-set time period upon failing to identify atrial fibrillation of intermediate disorganization during said pre-set time period.

8. An atrial cardiovertor/defibrillator as defined in claim 1 wherein the therapy means includes an atrial cardiovertor, wherein said classifying means causes said atrial cardiovertor to apply cardioverting electrical energy to the atria at a low energy level upon identifying atrial flutter and to cause said atrial cardiovertor to apply cardioverting electrical energy at an intermediate energy level upon identifying atrial fibrillation of intermediate disorganization, said intermediate energy level being greater in energy than said low energy level.

9. An atrial cardiovertor/defibrillator as defined in claim 8 wherein said classifying means causes said atrial cardiovertor to apply cardioverting electrical energy to the atria at a high energy level upon identifying atrial fibrillation of high disorganization, said high energy level being greater in energy than said intermediate energy level.

10. An atrial cardiovertor/defibrillator as defined in claim 9 further including first means for causing said cardiovertor to delay the application of the high energy level cardioverting energy for a pre-set time period.

11. An atrial cardiovertor/defibrillator as defined in claim 10 further including second means for activating said classifying means at predetermined times during said pre-set time period, said classifying means causing said cardiovertor to apply said intermediate energy level cardioverting energy upon identifying, during said pre-set time period, atrial fibrillation of intermediate disorganization and causing said cardiovertor to apply said high energy level cardioverting energy at the end of said pre-set time period upon failing to identify atrial fibrillation of intermediate disorganization during said pre-set time period.

12. An atrial cardiovertor/defibrillator as defined in claim 1 further including means for activating said classifying means for identifying atrial fibrillation of intermediate disorganization in response to said classifying means identifying atrial fibrillation of high disorganization.

13. An atrial cardiovertor/defibrillator as defined in claim 12 wherein the therapy means includes an atrial cardiovertor, wherein said classifying means causes said atrial cardiovertor to apply cardioverting electrical energy to the atria at an intermediate energy level upon identifying atrial fibrillation of intermediate disorganization.

14. An atrial cardiovertor/defibrillator as defined in claim 13 wherein said classifying means causes said atrial cardiovertor to apply cardioverting electrical energy to the atria at a high energy level upon failing to identify atrial fibrillation of intermediate disorganization after a pre-set time period, said high energy level being greater in energy than said intermediate energy level.

15. An atrial defibrillator comprising:

criteria establishing means for providing a respective different criteria for each of different types of atrial fibrillation;

a sensor for sensing activity of at least one of the atria of a heart to provide an electrogram signal;

therapy means for providing a corresponding therapy to the heart for each of said different types of atrial fibrillation; and classifying means responsive to said electrogram signal and said criteria establishing means for identifying one of said types of atrial fibrillation and causing said therapy means to provide the therapy to the heart corresponding to said identified one of said types of atrial fibrillation.

16. An atrial defibrillator as defined in claim 15 wherein said sensor includes means for sensing localized activity of the at least one of the atria of the heart.

17. An atrial defibrillator as defined in claim 16 wherein said sensor includes a pair of closely spaced sensing electrodes.

18. An atrial defibrillator as defined in claim 15 further including means for determining atrial cardiac cycle length and wherein the respective different criteria are based upon atrial cardiac cycle length.

19. An atrial defibrillator as defined in claim 18 further including means for determining atrial cardiac cycle length variability and wherein the respective different criteria are further based upon atrial cardiac cycle length variability.

20. An atrial defibrillator as defined in claim 15 wherein the respective different criteria include a first criteria for atrial fibrillation of intermediate organization, and a second criteria for atrial fibrillation of high disorganization.

21. An atrial defibrillator as defined in claim 20 wherein the therapy means comprises an atrial cardiovertor.

22. An atrial defibrillator as defined in claim 21 wherein said classifying means causes said cardiovertor to apply cardioverting electrical energy to the atria upon identifying atrial fibrillation of intermediate disorganization.

23. An atrial defibrillator as defined in claim 22 wherein said cardioverting energy is an intermediate level of energy and wherein said classifying means causes said cardiovertor to apply cardioverting energy at a high energy level upon identifying atrial fibrillation of high disorganization, said high energy level being greater in energy than said intermediate energy level.

24. An atrial defibrillator as defined in claim 23 further including first means for causing said cardiovertor to delay the application of the high energy level cardioverting energy for a pre-set time period.

25. An atrial defibrillator as defined in claim 24 further including second means for activating said classifying means at predetermined times during said pre-set time period, said classifying means causing said cardiovertor to apply said intermediate energy level cardioverting energy upon identifying, during said pre-set time period, atrial fibrillation of intermediate disorganization and causing said cardiovertor to apply said high energy level cardioverting energy at the end of said pre-set time period upon failing to identify atrial fibrillation of intermediate disorganization during said pre-set time period.

26. An atrial defibrillator as defined in claim 20 further including means for activating said classifying means for identifying atrial fibrillation of intermediate disorganization in response to said classifying means identifying atrial fibrillation of high disorganization.

27. An atrial defibrillator as defined in claim 26 wherein said classifying means causes said cardiovertor to apply cardioverting electrical energy to the atria upon identifying atrial fibrillation of intermediate disorganization.

28. An atrial defibrillator as defined in claim 27 wherein said cardioverting energy is an intermediate level of energy and wherein said classifying means causes said cardiovertor to apply cardioverting energy at a high energy level upon failing to identify atrial fibrillation of intermediate disorganization during a pre-set time period, said high energy level being greater in energy than said intermediate energy level.

29. A method of administering electrotherapy to the atria of a patient's heart to restore a normal atrial rhythm, said method comprising the steps of:

establishing a respective different criteria for each of different types of atrial arrhythmia;

sensing activity of at least one of the atria of the patient's heart to provide an electrogram signal;

applying said electrogram signal to each said criteria identify one of said types of atrial arrhythmia; and applying electrotherapy to the heart in a manner corresponding to the identified one of said types of atrial arrhythmia, wherein the respective different criteria include a first criteria for atrial flutter, a second criteria for atrial fibrillation of intermediate organization, and a third criteria for atrial fibrillation of high disorganization.

30. A method as defined in claim 29 wherein said second applying step includes pacing the atria upon identifying atrial flutter.

31. A method as defined in claim 30 wherein said second applying step includes applying cardioverting electrical energy to the atria at an intermediate energy level upon identifying atrial fibrillation of intermediate disorganization.

32. A method as defined in claim 31 wherein said second applying step includes applying cardioverting electrical energy to the atria at a high energy level upon identifying atrial fibrillation of high disorganization, said high energy level being greater in energy than said intermediate energy level.

33. A method as defined in claim 32 further including the step of delaying the application of the high energy level cardioverting energy for a pre-set time period.

34. A method as defined in claim 33 further including the step of re-identifying the atrial arrhythmia type during said pre-set time period, applying said intermediate energy level cardioverting energy upon identifying, during said pre-set time period, atrial fibrillation of intermediate disorganization and applying said high energy level cardioverting energy at the end of said pre-set time period upon failing to identify atrial fibrillation of intermediate disorganization during said pre-set time period.

35. A method as defined in claim 29 wherein said second applying step includes applying cardioverting electrical energy to the atria at a low energy level upon identifying atrial flutter, and applying cardioverting electrical energy to the atria at an intermediate energy level upon identifying atrial fibrillation of intermediate disorganization, said intermediate energy level being greater in energy than said low energy level.

36. A method as defined in claim 35 wherein said second applying step further includes applying cardioverting electrical energy to the atria at a high energy level upon identifying atrial fibrillation of high disorganization, said high energy level being greater in energy than said intermediate energy level.

37. A method as defined in claim 36 further including the step of delaying the application of the high energy level cardioverting energy for a pre-set time period.

38. A method as defined in claim 37 further including the step of re-identifying the atrial arrhythmia type during said pre-set time period, applying said intermediate energy level cardioverting energy upon identifying, during said pre-set time period, atrial fibrillation of intermediate disorganization and applying said high energy level cardioverting energy at the end of said pre-set time period upon failing to identify atrial fibrillation of intermediate disorganization during said pre-set time period.

39. A method as defined in claim 29 further including the step of re-identifying the atrial arrhythmia type for atrial fibrillation of intermediate disorganization after identifying atrial fibrillation of high disorganization.

40. A method as defined in claim 29 wherein said second applying step includes applying cardioverting electrical energy to the atria at an intermediate energy level upon identifying atrial fibrillation of intermediate disorganization.

41. A method as defined in claim 30 wherein said second applying step further includes applying cardioverting electrical energy to the atria at a high energy level upon failing to identify atrial fibrillation of intermediate disorganization during a pre-set time period.

42. A method of administering electrotherapy to the atria of a patient's heart to restore a normal atrial rhythm from fibrillation, said method comprising the steps of:

establishing a respective different criteria for each of different types of atrial fibrillation;

sensing activity of at least one of the atria of the patient's heart to provide an electrogram signal;

comparing at least one characteristic of said electrogram signal to each said criteria and identifying from the comparison one of said types of atrial fibrillation; and, applying electrotherapy to the heart in a manner corresponding to the identified one of said types of atrial fibrillation.

43. A method as defined in claim 42 wherein said sensing step includes sensing localized activity of the at least one of the atria of the heart.

44. A method as defined in claim 43 wherein said sensing step includes sensing said localized activity between a pair of closely spaced locations of the at least one of the atria.

45. A method as defined in claim 42 wherein said comparison step includes determining atrial cardiac cycle length from said electrogram signal and wherein the respective different criteria are based upon atrial cardiac cycle length.

46. A method as defined in claim 45 wherein said comparing step further includes determining atrial cardiac cycle length variability and wherein the respective different criteria are further based upon atrial cardiac cycle length variability.

47. A method as defined in claim 46 wherein the respective different criteria include a first criteria for atrial fibrillation of intermediate organization, and a second criteria for atrial fibrillation of high disorganization.

48. A method as defined in claim 47 wherein said applying step includes applying cardioverting electrical energy to the atria upon identifying atrial fibrillation of intermediate disorganization.

49. A method as defined in claim 48 wherein said cardioverting energy is an intermediate level of said energy and wherein said applying step includes applying cardioverting electrical energy to the atria at a high energy level upon identifying atrial fibrillation of high disorganization, said high energy level being greater in energy than said intermediate energy level.

50. A method as defined in claim 49 further including the step of delaying the application of the high energy level cardioverting energy for a pre-set time period.

51. A method as defined in claim 50 further including the step of re-identifying the atrial arrhythmia type classifying during said pre-set time period, applying said intermediate energy level cardioverting energy upon identifying, during said pre-set time period, atrial fibrillation of intermediate disorganization and applying said high energy level cardioverting energy at the end of said pre-set time period upon failing to identify atrial fibrillation of intermediate disorganization during said pre-set time period.

52. A method as defined in claim 47 further including the step of re-identifying the atrial arrhythmia type for atrial fibrillation of intermediate disorganization after identifying atrial fibrillation of high disorganization.

53. A method as defined in claim 52 wherein said applying step includes applying cardioverting electrical energy to the atria upon identifying atrial fibrillation of intermediate disorganization.

54. A method as defined in claim 53 wherein said cardioverting energy is an intermediate level of said energy and wherein said applying step includes applying cardioverting electrical energy to the atria at a high energy level upon failing to identify atrial fibrillation of intermediate disorganization during a pre-set time interval, said high energy level being greater in energy than said intermediate energy level.

55. An atrial cardiovertor/defibrillator comprising:

criteria establishing means for providing a respective different criteria for each of different types of atrial arrhythmia;

a sensor for sensing activity of at least one of the atria of a heart to provide an electrogram signal;

therapy means for providing a corresponding therapy to the heart for each of said different types of atrial arrhythmia; and classifying means responsive to said electrogram signal and said criteria establishing means for identifying one of said types of atrial arrhythmia and causing said therapy means to provide the therapy to the heart corresponding to said identified one of said types of atrial arrhythmia, wherein the respective different criteria include criteria for atrial fibrillation of intermediate organization and criteria for atrial fibrillation of high disorganization.

56. A method of administering electrotherapy to the atria of a patient's heart to restore a normal atrial rhythm, said method comprising the steps of:

establishing a respective different criteria for each of different types of atrial arrhythmia;

sensing activity of at least one of the atria of the patient's heart to provide an electrogram signal;

applying said electrogram signal to each said criteria to identify one of said types of atrial arrhythmia; and applying electrotherapy to the heart in a manner corresponding to the identified one of said types of atrial arrhythmia, wherein the respective different criteria include criteria for atrial fibrillation of intermediate organization and criteria for atrial fibrillation of high disorganization.

* * * * *